(12) United States Patent
Doyle et al.

(10) Patent No.: US 6,183,977 B1
(45) Date of Patent: Feb. 6, 2001

(54) DETERMINING HEPATIC STATUS OF A LIVER TRANSPLANT RECIPIENT BY MEASURING PI GLUTATHIONE S-TRANSFERASE

(75) Inventors: John Martin Doyle, Deansgrange; Cormac Gerard Kilty, Sandycove; Fiona Mary Manning, Lusk, all of (IE)

(73) Assignee: Biotrin Intellectual Properties, Ltd., County Dublin (IE)

( * ) Notice: Under 35 U.S.C. 154(b), the term of this patent shall be extended for 0 days.

(21) Appl. No.: 09/117,476

(22) PCT Filed: Feb. 2, 1996

(86) PCT No.: PCT/IE96/00003

§ 371 Date: Jul. 31, 1998

§ 102(e) Date: Jul. 31, 1998

(87) PCT Pub. No.: WO97/28449

PCT Pub. Date: Aug. 7, 1997

(51) Int. Cl.[7] .................... G01N 33/53; G01N 33/543; A01N 1/02; C12Q 1/48
(52) U.S. Cl. .............. 435/7.9; 435/2; 435/7.94; 435/15; 435/975
(58) Field of Search ................... 435/2, 7.1, 7.4, 435/7.9, 7.94, 15, 975

(56) References Cited

U.S. PATENT DOCUMENTS

Re. 35,419 * 1/1997 Kilty et al. ..................... 435/7.4

FOREIGN PATENT DOCUMENTS

| 4025763A | 1/1992 | (JP) . |
| WO9012088 | 10/1990 | (WO) . |
| WO9322452 | 11/1993 | (WO) . |

OTHER PUBLICATIONS

Chemical Abstracts, vol. 109, No. 25, Abstract No.: 225320 (Dec. 19, 1988).
Chemical Abstracts, vol. 118, No. 9, Abstract No.: 78246 (Mar. 1, 1993).
Chemical Abstracts, vol. 117, Abstract No.: 231211 (Dec. 7, 1992).

* cited by examiner

*Primary Examiner*—David M. Naff
(74) *Attorney, Agent, or Firm*—Birch, Stewart, Kolasch & Birch, LLP.

(57) ABSTRACT

Hepatic status of a subject is determined by measuring the level of pi glutathione S-transferase (πGST) in a biological fluid such as bile or plasma from the subject by an immunoassay. An increased level of πGST as compared to a normal range of πGST indicates an abnormal condition of the liver. Measuring πGST level has particular application for determining the hepatic status of a liver transplant recipient because it enables detecting liver transplant rejection at a very early stage after transplantation. The immunoassay is preferably an enzyme immunoassay, and the entire immunoassay can be completed in 2.5 hours. The biological fluid may be diluted with a diluent which contains an effective amount of a protein such as serum albumin to optimize antibody-antigen reaction. When plasma is the fluid, the plasma should be collected and stored prior to the determination in the presence of an anti-coagulant under conditions which permit substantially no haemolysis. The level of alpha glutathione S-transferase (αGST) may also be determined in biological fluid from the subject to facilitate differentiation between graft rejection and non-specific hepatocellular damage.

10 Claims, 7 Drawing Sheets

DETERMINING HEPATIC STATUS OF A LIVER TRANSPLANT RECIPIENT BY MEASURING PI GLUTATHIONE S-TRANSFERASE

This application is the national phase under 35 U.S.C. §371 of prior PCT International Application No., PCT/IE96/00003, which has an International filing date of Feb. 2, 1996, which designated the United States of America, the entire contents of which are hereby incorporated by reference.

TECHNICAL FIELD

This invention relates to a method of determining the hepatic status of a subject, including a liver transplant recipient and, thereby, deciding on appropriate therapy or corrective action, if required, dependent on said hepatic status.

BACKGROUND ART

The ability to differentiate between the various types of hepatic injury is of great significance in the treatment of both transplant patients and also individuals who suffer from other hepatic diseases which may affect the biliary system.

Glutathione S-transferases (GSTs) comprise a multigene family of proteins consisting mainly of alpha ($\alpha$GST), mu ($\mu$GST), pi ($\pi$GST) and theta-class ($\theta$GST) isoforms as defined by isoelectric point and are responsible for the detoxification of a range of xenobiotics, mainly via conjugation to glutathione (Beckett, G. J and Hayes, J. D., Advances in Clinical Chemistry (1993); 30, 281–380). Generally, the proteins are dimeric in nature consisting of two 25–27kDa subunits and may exist in homodimeric or heterodimeric forms. Pi Glutathione S-transferase ($\pi$GST) is a homodimer, and is located in the cytoplasm of bile duct epithelial cells within the liver (Beckett G. J. and Hayes, J. D., (1993) supra). $\alpha$GST is known to be present in hepatocytes within the liver and exists in both homodimeric and heterodimeric states (Campbell, J. A. H., et. al., Cancer (Philadelphia) (1991) 67, 1608–1613; Howie, A. F., et. al., Clin. Chem. Acta., (1988) 177, 65–76). This heterogenous GST distribution of $\alpha$ and $\pi$GST suggests that the different isoenzymes have unique in vivo functions in different hepatic regions (Campbell, J. A. H., et. al., (1991) supra).

EP-A 0 640 145 discloses a method which assists in the early diagnosis of rejection in a liver transplant recipient and which comprises measuring an increase in plasma or serum $\alpha$GST from the recipient in the absence of or preceding any change in plasma or serum transaminase. Thus, it has been conclusively demonstrated that measurement of the plasma $\alpha$GST level facilitates monitoring of the post-transplant hepatic status by acting as an extremely sensitive, although not totally specific marker of graft rejection.

It is notable that $\pi$GST has received no attention as a potential marker of graft rejection, a fact possibly due to the low levels of enzyme present in the biliary epithelial cells of the liver. There is some evidence, however, that $\alpha$ and $\pi$GST are present in bile from both normal individuals and people suffering from specific cancers (e.g., cholangiocarcinoma) as measured by radio-immunoassay (Howie. A. F., et. al., Clin. Chem. Acta. (1989) 184, 269–278). Additionally, some authors have referenced the fact that measurement of serum and plasma $\pi$GST levels may facilitate diagnosis of malignant tumours since $\pi$GST appears to be specifically expressed in malignant tissue (Niitsu, Y., etal., Cancer (1989) 63, 317–323; Howie, A. F., et. al., Clin. Chem. (1990) 36(3), 453–456. and Hida, T., et al., Cancer (1994) 73(5), 1377–1382. None of the aforementioned authors allude to the fact that $\pi$GST may have a role in the prediction of transplanted liver rejection or other liver/biliary disorders.

Since it is known that primary graft rejection generally occurs in the biliary tree within the liver (Ascher, N., (1993) In 'Immunology of liver transplantation' Neuberger, J. and Adams, D. (eds)), it would appear that specific measurement of biliary or plasma $\pi$GST levels may allow diagnosis of early rejection or facilitate discrimination between post-transplant hepatocellular or biliary damage. The importance of distinguishing between non-specific hepatic injury and graft rejection cannot be overstated since the treatment for each condition is entirely different. Furthermore, initiation of the incorrect treatment could be extremely deleterious to the health of an individual already severely ill. For example, if graft injury occurs due to viral infection (e.g., Hepatitis C re-infection or cytomegalovirus (CMV), it is necessary to carefully monitor the levels of anti-rejection immunosuppression treatment since excess immunosuppresive agents (e.g., cyclosporin A or FK506) would significantly impair the ability to fight viral infection. Conversely, failure to recognise genuine rejection from non-specific graft injury could lead to delay in augmentation of immunosuppressive therapy and ultimately lead to graft removal.

Accordingly, there is a need for methods of determining the hepatic status of an individual in various disease states or abnormal conditions of the liver.

SUMMARY OF THE INVENTION

The invention provides a method of determining the hepatic status of a subject, which method comprises measuring the level of the pi glutathione S-transferase ($\pi$GST) isoform in a sample of a biological fluid from said subject by an immunoassay specific for the $\pi$GST isoform, comparing the level of $\pi$GST measured with the normal range of $\pi$GST in said biological fluid and, when an increase in $\pi$GST level relative to said normal range is detected, determining the hepatic status of the subject based on the level of $\pi$GST in said biological fluid.

By providing a further method for determining hepatic status based on a marker specific to a particular hepatic site greatly facilitates the treatment of patients with various disease states and other abnormal conditions of the liver as hereinafter described in greater detail.

The subject is suitably a liver transplant recipient and the hepatic status is determined post-transplantation.

The invention has particular application in the case of liver transplantation because it enables one to determine at a very early stage post-transplantation a likelihood of rejection because the primary graft rejection generally occurs in the biliary tree within the liver as stated above. Accordingly, even earlier detection of liver transplant rejection is possible with the method according to the invention relative to the method described and claimed in EP-A 0 640 145.

Preferably, the recipient is a human.

The immunoassay is preferably an enzyme immunoassay, more especially a sandwich enzyme immunoassay.

The method according to the invention can be used to measure $\pi$GST in a range of media, but especially in bile, plasma and serum.

By biological fluid herein is meant for example body fluids such as bile, plasma, serum and urine as well as tissue support media and perfusates. The biological fluids herein are also referred to generally as matrices.

The method according to the invention facilitates for the first time detection of the $\pi$GST isoenzyme level in bile.

When the biological fluid is bile, the normal πGST level is less than 15 μg/L.

When the biological fluid is plasma, the normal πGST level is less than 100 μg/L.

As demonstrated hereinbelow care should be taken when the method is carried out on plasma that the plasma is collected and stored prior to the determination in the presence of an anti-coagulant under conditions which permit substantially no haemolysis to occur during said storage period.

We have found that use of fluoro-oxylate tubes results in a high degree of haemolysis releasing πGST from erythrocytes which gives falsely elevated levels of πGST. Other GST isoenzymes are either not found in the blood or are present at extremely low levels. For example, μGST is present in leucocytes. However, it is not clear from the literature as to whether it is present in erythrocytes. In any event μGST is only present in 50% of the population. θGST expresses a similar inter-individual variability as does μGST and if present in blood is present at extremely low levels. αGST is not present in blood to any great extent.

In a preferred embodiment, the sample is diluted with a diluent which contains an effective amount of a protein which optimises antibody-antigen reactions.

We have found that if the diluent includes Tween 20 conventionally used as a standard reagent in such immunometric methods that incorrect πGST concentrations are detected. We have found that if one uses an effective amount of a protein which optimises antibody-antigen reactions, one can achieve a linear titration as shown in Example 6.

Suitably, the protein is a serum albumin such as bovine serum albumin or human serum albumin.

The immunoassay method according to the invention can be completed within 2.5 hours as hereinafter described in Examples. This is considerably faster than any commercially available assay for the quantitation of πGST.

The invention thus provides in one embodiment an immunoassay capable of being completed in under 2.5 hours which is based on the sequential addition of sample, antibody-enzyme conjugate and substrate to microtitre wells or other surface coated with monoclonal anti-πGST IgG. The resultant colour intensity is proportional to the amount of πGST present in the sample and the assay range is 0–100 μg/L. The assay range is readily extended by increased sample dilution.

According to another embodiment of the invention, additionally the level of the alpha glutathione S-transferase (αGST) isoform is measured in a sample of a biological fluid from said subject so as to facilitate differentiation between graft rejection and non-specific hepatocellular damage in said subject.

The invention also provides a test kit or pack containing one or more components for carrying out a method as hereinabove defined.

DETAILED DESCRIPTION OF THE INVENTION

Figure 1:
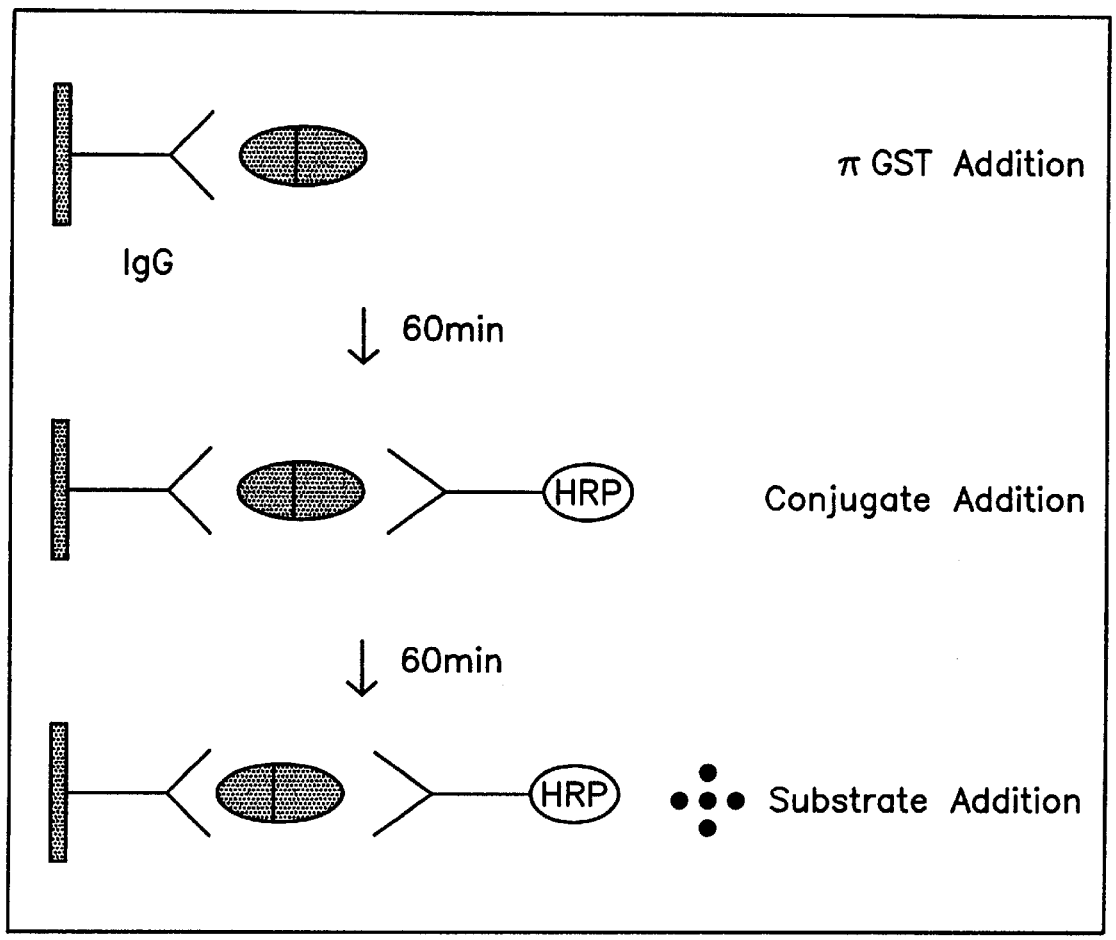
FIG. 1 is a schematic diagram of the sandwich enzyme immunoassay of Example 1.

The invention will be further illustrated by the following Examples.

PREPARATORY EXAMPLE A

Purification of human πGST

πGST was purified from human placenta by affinity chromatography. Precise details of the purification procedure are as follows:

a. 325 g of human placenta was homogenised for 2 minutes in homogenisation buffer, at a ratio of one part placenta to three parts buffer, using a Waring (Waring is a Trade Mark) blender. The homogenisation buffer had the following composition:
20 mM Tris-HCl
250 mM Sucrose
5 mM EDTA pH 7.8
2 μg/ml Leupeptin
2 μg/ml Pepstatin.

b. The placenta homogenate was centrifuged at 10000 g for 60 minutes.

c. The supernatant was then loaded on a Glutathione (GSH)-Sepharose Affinity column previously equilibrated in 20 mM Tris-HCl with 200 mM NaCl, pH 7.8. Equilibration buffer was reapplied to elute unbound protein. Finally 50 mM Tris-HCl pH 9.5 containing 5 mM GSH was used to elute bound GST from the affinity column.

d. The eluted material was then dialysed against 0.1M PBS.

PREPARATORY EXAMPLE B

Antibody Production and Purification:

Purified human πGST was injected into New Zealand White rabbits subcutaneously (s.c.) according to the time schedule given below and serum evaluated for anti-πGST reactivity. Once the IgG [anti-human πGST] titre was sufficient as determined by semi-quantitative dot blot analysis, the animals were exsanguinated and serum collected. Total IgG was purified from rabbit serum by Protein A affinity chromatography and was used for conjugation to horseradish peroxidase (HRP). Monoclonal IgG [anti-human πGST] as ascites, was obtained from The University Hospital, Nijmegen, The Netherlands and was not purified further prior to use.

Immunisation Schedule (general):

Day 1: A test bleed of 8 ml of preserum was taken from the ear of the rabbit. 0.5 ml of human πGST antigen (100 μg) was mixed with an equal volume of Freund's Complete Adjuvant. The mixture of antigen and adjuvant was homogenised to ensure a good emulsion. This mixture was then injected subcutaneously into multiple sites on the back of the rabbit which had previously been shaved.

Day 28: A test bleed of 5 ml of serum was taken from the ear of the rabbit. 0.5 ml antigen (100 μg) was mixed with an equal volume of Freund's Incomplete Adjuvant. The antigen/adjuvant mixture was homogenised to ensure a good emulsion. This mixture was then injected subcutaneously into multiple sites on the back of the rabbit.

Day 42: A test bleed of 10 ml of blood was taken from the rabbit's ear.

Day 56: A second boost was given to the rabbit as described on Day 28.

Day 70: A test bleed of 10 ml of blood was taken from the ear of the rabbit. When the titre was sufficiently high, the rabbit was sacrificed and as much blood as possible collected.

PREPARATORY EXAMPLE C

Immunoblotting:

All polyclonal and monoclonal IgGs for use in the followings Examples were checked for πGST reactivity and potential cross-reactivity against human α and μGST respectively, via the following immunoblot combinations:

(a) Rabbit IgG [anti-human πGST] was used to probe nitrocellulose membranes containing immobilised human α, π and μGST.

(b) Murine IgG [anti-human πGST] was used to probe nitrocellulose membranes containing immobilised human α, π and μGST.

The method used for immunoblot detection was as follows:

1. Human α, π and μGST (0.5 μg/track) were electrophoresed on 15% SDS-PAGE with molecular weight markers also included.

2. After electrophoresis, the polyacrylamide gel was cut and one half stained for protein while the remainder was used for electrophoretic transfer onto nitrocellulose.

3. After electrophoretic transfer, the nitrocellulose membranes were blocked for 1 hour with 5%(w/v) Marvel (Marvel is a Trade Mark) in phosphate buffered saline containing 0.05%(w/v) TWEEN-20 (PBST)-blocking buffer.

4. The following solutions were then prepared:
   (i) Rabbit IgG [anti-human πGST] in 1%(w/v) Marvel in PBST
   (ii) Murine IgG [anti-human πGST] in 1%(w/v) Marvel in PBST and added to the membranes once blocking buffer was decanted.

Incubation with antibody solutions was allowed to proceed for one hour.

5. The nitrocellulose membranes were then washed in PBST (2× for 5 min each).

6. Anti rabbit IgG-HRP conjugate was then prepared (1/1000 in 1% (w/v) Marvel in PBST and added to 4(i) above. Anti murine IgG-HRP conjugate was also prepared (1/1000) and added to 4(ii) above.

7. After one hour incubation with anti-species conjugates, the reagents were discarded and the membranes washed as in 5 above.

8. Diaminobenzidine substrate was then prepared and added to the membrane.

A positive reaction was indicated by a brown precipitate on the nitrocellulose membrane.

PREPARATORY EXAMPLE D

Anti πGST IgG-horseradish peroxidase (HRP) conjugate synthesis:

Anti πGST IgG-HRP conjugates were synthesised using thioether conjugation methodology. (Duncan, R. J. S., et al., (1983); Anal. Biochem. 132, 68–73) Reactive maleimide groups were introduced onto IgG molecules using SMCC (succinimidyl 4-(N-maleimidomethyl) cyclohexane 1-carboxylate) and masked sulphydryl groups were linked to HRP. After a demasking step to produce reactive sulphydryl groups, the maleimide-activated IgG and HRP-SH were mixed together and allowed to react for 4.5 hours. The resultant IgG-HRP conjugate. formed by covalent thioether linkage, was brought to 50% (v/v) glycerol and stored at −20° C. for use in the EIA of Example 1.

EXAMPLE 1

Sandwich Enzyme Immunoassay

Figure 2:
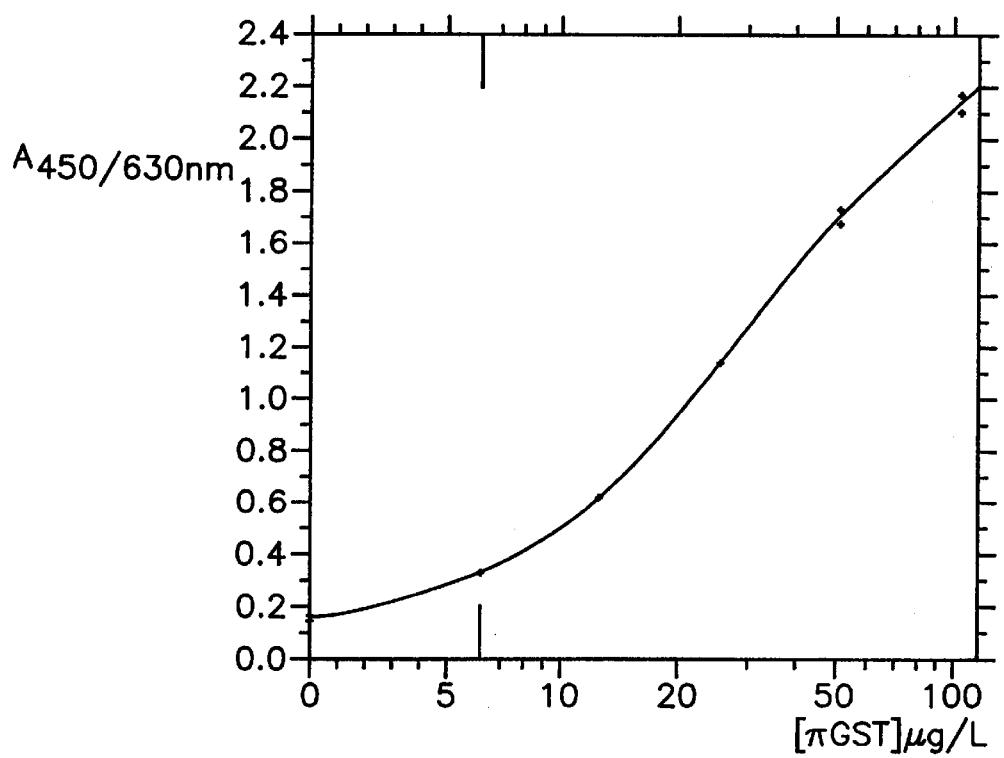
FIG. 2 is a plot of absorbance at 450/630 nm versus log πGST concentration (μg/L) according to the enzyme immunoassay for human πGST described in Example 1.

The format of the immunoassay for the quantitative detection of human πGST is a conventional sandwich format as depicted schematically in FIG. 1, and described below.

a. A Nunc Maxisorp (Nunc Maxisorp is a Trade Mark) microtitre plate was coated with murine monoclonal IgG [anti-human πGST] (referred to in Preparatory Example B) immobilised via goat $F(ab)_2$ fragments [anti-mouse IgG]. This method of antibody coating serves to orientate Mab binding sites and also improves assay sensitivity by minimising adherence—induced denaturation of the capture antibody.

b. Human πGST, purified from placenta as described in Preparatory Example A, was used as the assay calibrator.

c. IgG [anti-human πGST]-HRP conjugates, in association with tetramethylbenzidine substrate (TMB), were used to facilitate detection of captured/immobilised πGST.

d. The enzyme reaction was stopped by the addition of 1N $H_2SO_4$ and the absorbance measured at 450 nm using 630 nm as a reference wavelength. Colour intensity was proportional to πGST concentration and after generating a plot of $A_{450/630\ nm}$ versus concentration (μg/L), the concentration of unknown samples can be determined (see FIG. 2). Total assay time was less than 2.5 hours.

The total assay time was found to be 2 hours 15 minutes and assay conditions included microtitre plate shaking at fixed temperature during the sample and conjugate incubation steps, respectively. The TMB substrate incubation required fixed temperature conditions only.

EXAMPLE 2

Collection of Plasma for πGST Analysis

The effect of a variety of commonly used anti-coagulants (ethylenediaminetetraacetic acid (EDTA), lithium heparin, sodium citrate and fluoro-oxylate) and other plasma collection tubes (containing platelet inhibitors) on πGST levels in plasma, was examined. Samples were collected by venipuncture into tubes containing the particular anticoagulant. Plasma was separated by centrifugation (6,000 g for 10 min), and residual platelets were removed by an additional centrifugation step (10,000 g for 10 min). The supernatant was removed, and samples were assayed using the protocol described in Example 1.

Plasma was collected from a number of individuals into a series of plasma collection tubes. Each sample was handled as described above, and the release of πGST into plasma was monitored over a 24 hour period. Table 1 below shows the πGST levels in plasma from the same individual collected into four different plasma collection tubes, assayed at T0 and T24. The results show that there is no significant difference in πGST concentrations in plasma collected in the presence of any of the above anti-coagulants. There does not appear to be a significant increase in πGST concentrations (caused by release of πGST from erythrocytes or platelets) when the unseparated plasma is stored for up to 24 hours. The exception is the fluoro-oxylate tubes where a large degree of haemolysis occurred, releasing πGST from erythrocytes, and giving falsely elevated levels of the protein as shown in Table 1.

TABLE 1

Comparison of the influence of anti-coagulants in plasma collection tubes for πGST analysis in plasma. Values are given in µg/L.

| Patient | EDTA | | Li/Hep | | Na citrate | | Fl oxylate | |
|---|---|---|---|---|---|---|---|---|
| | T0 | T24 | T0 | T24 | T0 | T24 | T0 | T24 |
| 1 | 171.9 | 220.2 | 199.4 | 194.7 | 167.5 | 220.3 | 170.0 | >500 |
| 2 | 65.6 | 70.5 | 62.8 | 88.4 | 53.2 | 65.4 | 55.4 | >500 |
| 3 | 59.6 | 78.6 | 65.4 | 88.6 | 53.7 | 68.4 | 59.9 | >500 |
| 4 | 81.7 | 92.8 | 90.2 | 119.5 | 74.9 | 122.1 | 81.2 | >500 |
| 5 | 46.7 | 67.5 | 44.6 | 73.3 | 28.9 | 68.6 | 60.9 | >500 |

It can be seen from Table 1 that there is no significant difference between the concentration of πGST in plasma collected in the presence of any of the above anti-coagulants.

EXAMPLE 3

Assessment of Purity of Immunoassay Reagents

Figure 3:
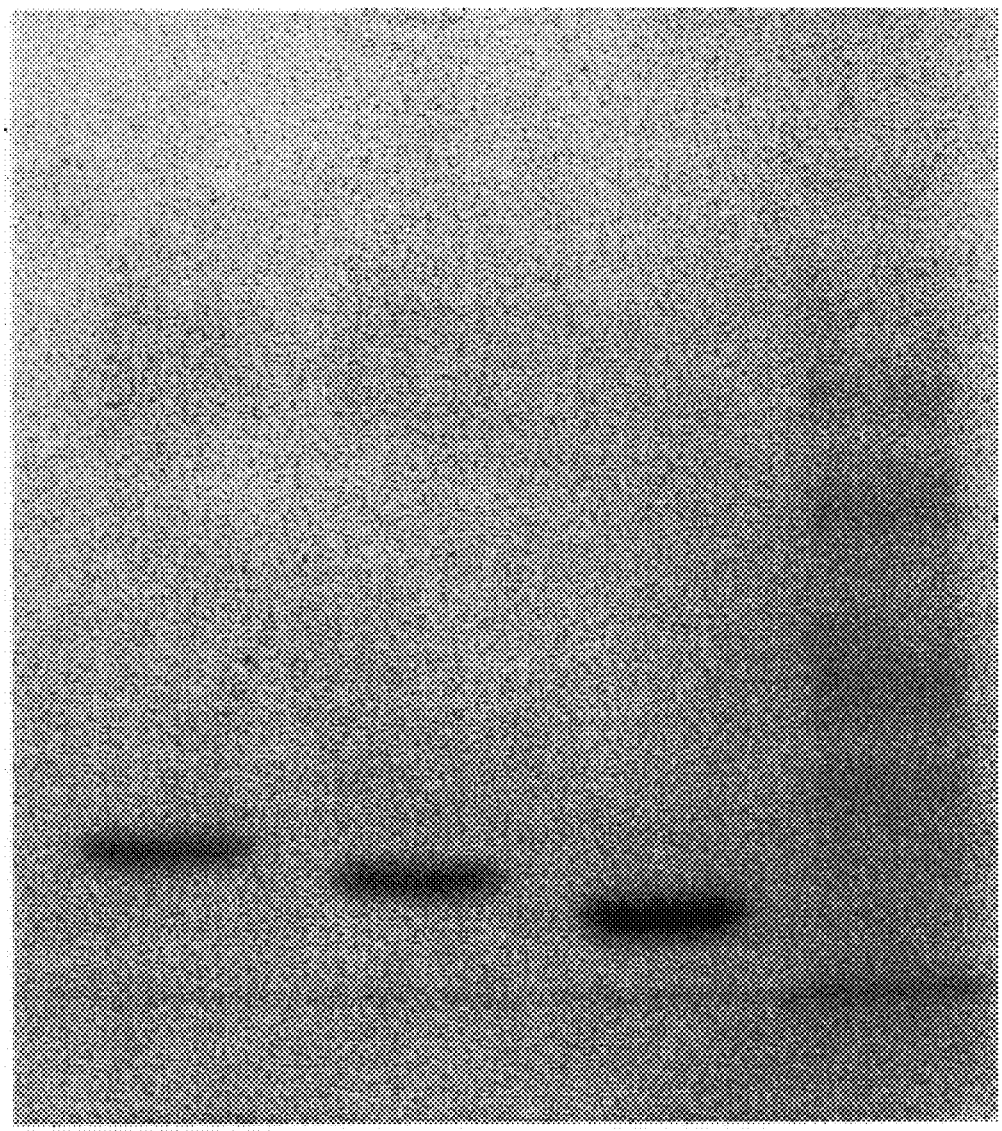
FIG. 3 is an SDS-PAGE analysis of human μ, α and πGST.

FIG. 3 illustrates the purity of human πGST obtained by the procedure of Preparatory Example A prior to immunisation into rabbits and confirms the absence of any other human derived proteins which might otherwise contribute to reduced assay specificity. In FIG. 3:

Lane 1=µGST

Lane 2=αGST

Lane 3=πGST

Lane 4=molecular weight markers.

Figure 4:
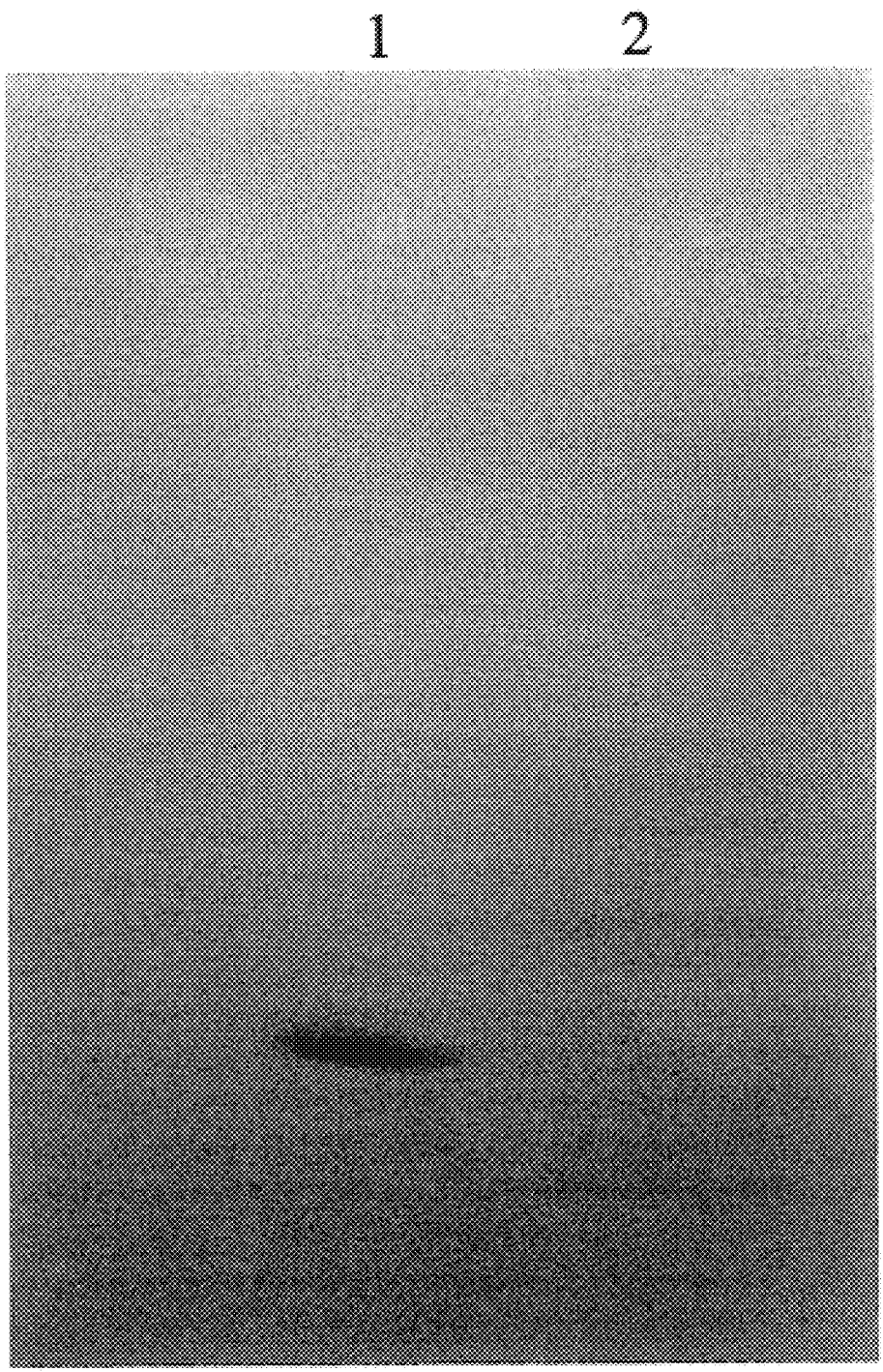
FIG. 4 is an immunoblot analysis of human πGST.

Immunoblot analysis of the monoclonal antibody reactivity revealed that the IgG[anti-human πGST] was highly specific for human πGST and did not exhibit any significant cross-reactivity with human α or µGST. The results are shown in FIG. 4.

Lane 1=πGST

Lane 2=molecular weight markers.

A finding supported by the lack of α and µGST reactivity in the human πGST-specific enzyme immunoassay as shown in Table 2.

TABLE 2

Evaluation of human αGST and µGST reactivity in the enzyme immunoassay for the detection of human πGST.

| GST Conc. | $A_{450/630\,nm}$ | | |
|---|---|---|---|
| | πGST | αGST | µGST |
| 0.00 | 0.022 | 0.022 | 0.022 |
| 3.12 | 0.087 | 0.024 | 0.016 |
| 12.5 | 0.299 | 0.020 | 0.022 |
| 25.0 | 0.688 | 0.036 | 0.055 |
| 50.0 | 1.204 | 0.018 | 0.034 |
| 100 | 1.735 | 0.040 | 0.043 |

It is clear from Table 2 that no cross-reactivity is evident for either αGST or µGST in this assay.

The significance of this fact is of utmost importance since it implies that the enzyme immunoassay for human πGST quantitation is specific for the detection of human πGST. Thus, any human πGST present in samples can be specifically detected without cross-contamination from other GSTs.

EXAMPLE 4

πGST Quantitation in Bile

A number of bile samples from patients with specific liver/biliary damage were tested in the assay for human πGST. Patients with hepatocellular carcinoma (HCC) and primary biliary cirrhosis (PBC) were found to contain very high levels of πGST. A patient with bile duct stones (BDS) was also found to have increased πGST levels, but not as elevated as those for HCC and PBC as shown in Table 3.

TABLE 3

πGST concentrations in bile from patients with hepatocellular carcinoma (HCC), primary biliary cirrhosis (PBC) and bile duct stone (BDS).

| Condition | [πGST] (µg/L) |
|---|---|
| HCC | 5357 |
| PBC | 2432 |
| BDS | 506.6 |

All of these samples show significantly elevated πGST levels.

EXAMPLE 5

Clinical Utility of πGST Quantitation

Serial bile and plasma samples were collected from patients following liver transplant operations and assayed for both π and αGST respectively. The patients exhibited a range of post-operative conditions, from uneventful recovery, to acute rejection and Hepatitis C re-infection, which are normally associated with transplantation.

Figure 5:
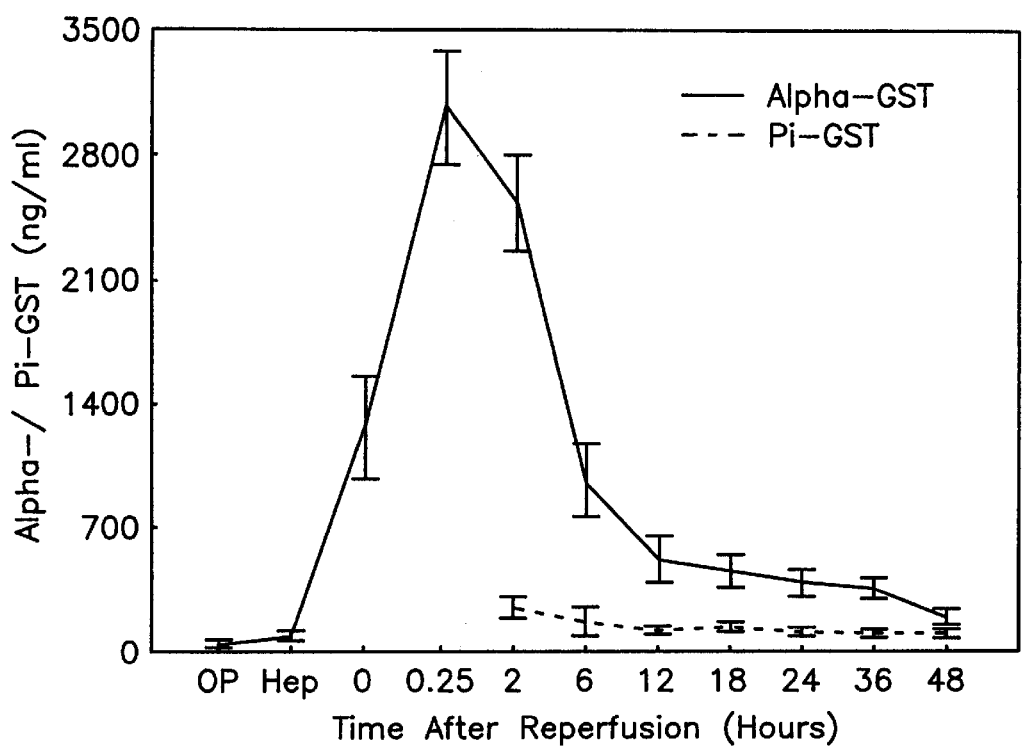
FIG. 5 is a plot of αGST and πGST (ng/ml) in bile versus time after reperfusion (hours) for a number of patients.
Figure 6:
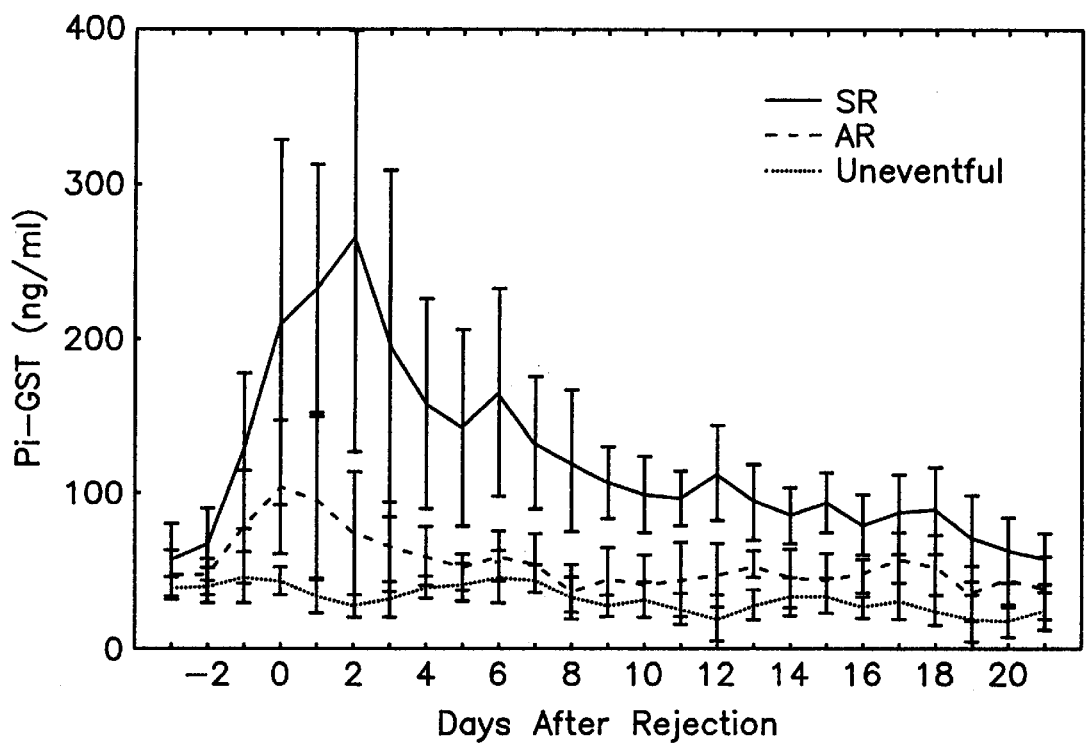
FIG. 6 is a plot of πGST concentration versus time (days) for a number of patients.

A number of significant trends were observed when the concentrations of both π and αGST in bile were monitored simultaneously. αGST was measured according to the procedure described in EP-A 0 640 145. During an uneventful recovery, πGST could be detected as soon as 2 hours post transplantation, and levels remained low (i.e. below 50 µg/L). αGST levels were initially high due to reperfusion injury, but returned to baseline levels within 2 days as shown in FIG. 5. This figure shows the typical course of α and πGST during and after human liver transplantation. πGST levels remain low. Complications associated with liver transplantation could also be identified. One of the major risks is acute rejection, or the even more serious, steroid-resistant rejection. We have found that in these particular cases, there was a significant increase in πGST levels sustained over a period of days as shown in FIG. 6. This figure shows πGST levels during episodes of steroid-resistant rejection (SR) and acute rejection (AR). Levels are elevated and remain high over a period of at least 20 days. αGST levels were also high, but they returned to baseline levels within a period of 5–8 days.

Figure 7:
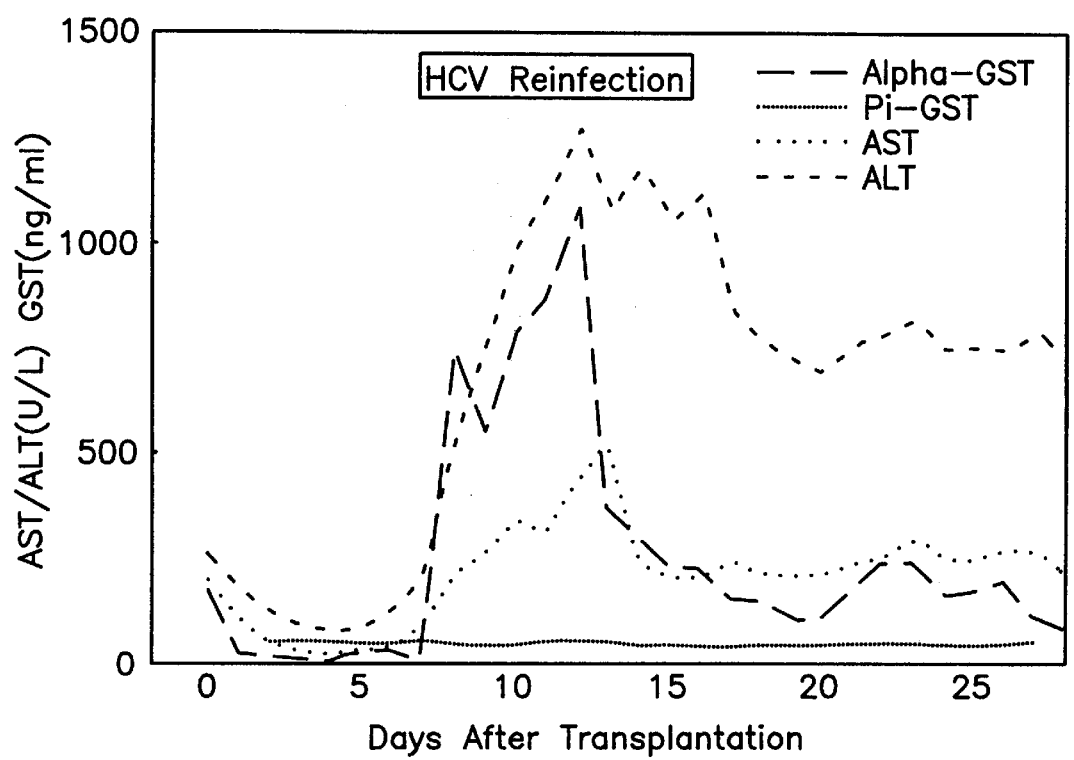
FIG. 7 is a plot of AST/ALT (U/L) and αGST and αGST (ng/ml) versus days after transplantation for a single patient.

The possibility of infection or re-infection is another serious risk involved in transplantation. We have seen that in episodes of HCV re-infection, very high levels of αGST were observed over a sustained period of time (i.e. at least 25 days). However, πGST levels remained near normal as shown in FIG. 7. This contrasts sharply with the previous cases of acute rejection, where the reverse was true. Thus, by the simultaneous quantitation of α and πGST, it was possible to successfully differentiate between acute rejection and HCV re-infection, something which has previously proved to be very difficult, and has posed a therapeutic dilemma to transplant surgeons.

EXAMPLE 6

Linearity of Dilution of Bile Samples

A number of bile samples were obtained from patients with specific liver/biliary damage (hepatocellular carcinoma and primary biliary cirrhosis), as well as samples from donor bile, and post liver transplantation. These samples were assayed for human πGST according to the protocol of Example 1.

A number of standard diluents were used as sample diluents for the titration of the bile samples. These diluents are routinely used in many assay systems, with Tween-20 being the most commonly used detergent. We have found however that the presence of this particular detergent in the sample diluent caused erroneous results. Falsely high concentrations of πGST were observed in samples diluted in Tween-20-containing containing diluents, caused by insufficient titration as shown in Table 4. In the absence of Tween-20, linear titration was observed. Therefore, a critical factor of this assay is the absence of Tween-20 (a standard reagent) in the sample diluent, as falsely elevated levels of πGST would be observed if it were used.

TABLE 4

Comparison of the titration of a PBC bile sample in diluents with and without Tween-20. Values are given in μg/L.

| Dilution | − Tween-20 | + Tween-20 |
|---|---|---|
| 1/50 | 2344 | 3074 |
| 1/100 | 2374 | 5187 |
| 1/200 | 2410 | 7059 |

Linear titration was observed only in the diluent without Tween-20.

EXAMPLE 7

Comparison of Polyclonal and Monoclonal Antibodies as Coating Antibodies

Polyclonal and monoclonal anti-human πGST IgG were immobilised onto Nunc Maxisorp plates either directly or via a linker (F(ab)$_2$ fragments of goat anti-species IgG). Standards of known concentrations of human πGST were then run as described in Example 1 and the absorbances at similar immobilised IgG concentrations compared.

Both polyclonal and monoclonal antibodies were coated onto the solid phase for use as a capture antibody. Direct coating of the both the polyclonal and the monoclonal antibodies resulted in very low absorbance readings for the standard curve (see Table 5). When immobilisation was achieved via a linker antibody (goat anti-mouse/anti-rabbit IgG), a significant increase in O.D. values was obtained for the monoclonal antibody. However, no such increase was observed for the polyclonal antibody.

TABLE 5

Comparison of coating methods for the detection of human πGST.

| [πGST] | DIRECT COATING | | COATING via LINKER ANTIBODY | |
|---|---|---|---|---|
| | Polyclonal | Monoclonal | Polyclonal | Monoclonal Ab. |
| 100 | 0.625 | 0.421 | 0.352 | 1.557 |
| 0 | 0.044 | 0.038 | 0.235 | 0.095 |

Direct coating of the antibody onto the solid phase (2 μg/mL) was compared to coating via a linker antibody (goat anti species, at 2 μg/ml), with the anti πGST antibody at a fixed concentration.

What is claimed is:

1. A method of determining the hepatic status of a liver transplant recipient after liver transplantation, which method comprises measuring the level of the pi glutathione S-transferase (πGST) isoform in a sample of a biological fluid from said liver transplant recipient by an immunoassay specific for the πGST isoform, comparing the level of πGST measured with the normal range of πGST in said biological fluid and, when an increase in πGST level relative to said normal range is detected, determining the hepatic status of said liver transplant recipient based on the level of πGST in said biological fluid.

2. A method according to claim 1, wherein the subject is a human.

3. A method according to claim 1, wherein the immunoassay is an enzyme immunoassay.

4. A method according to claim 1, wherein the biological fluid is bile and the normal πGST level is less than 15 μg/L.

5. A method according to claim 3, wherein the biological fluid is plasma and the normal πGST level is less than 100 μg/L.

6. A method according to claim 5, wherein the plasma is collected and stored prior to the determination in the presence of an anti-coagulant under conditions which permit substantially no haemolysis to occur during said storage period.

7. A method according to claim 1, wherein the sample is diluted with a diluent which contains an effective amount of a protein which optimises antibody-antigen reactions.

8. A method according to claim 7, wherein the protein is a serum albumin.

9. A method according to claim 1, wherein the entire immunoassay is completed within 2.5 hours.

10. A method according to claim 1, wherein additionally the level of the alpha glutathione S-transferase (αGST) isoform is measured in a sample of a biological fluid from said subject so as to facilitate differentiation between graft rejection and non-specific hepatocellular damage in said subject.

* * * * *